US00PP13832P29

(12) United States Plant Patent
Beckmann

(10) Patent No.: US PP13,832 P2
(45) Date of Patent: May 20, 2003

(54) POINSETTIA PLANT NAMED 'GIANT RED'

(76) Inventor: Rudolf Beckmann, Gartnersiedlung 16, 24610 Gönnebek (DE)

( * ) Notice: Subject to any disclaimer, the term of this patent is extended or adjusted under 35 U.S.C. 154(b) by 0 days.

(21) Appl. No.: 10/122,735

(22) Filed: Apr. 14, 2002

(51) Int. Cl.[7] ..... A01H 5/00
(52) U.S. Cl. ..... Plt./307

(58) Field of Search ..... Plt./307

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Poinsettia plant named 'Giant Red', characterized by its inflorescences with red-colored flower bracts; dark green-colored leaves; uniform and rounded plant habit; early flowering habit; and excellent post-production longevity.

1 Drawing Sheet

BOTANICAL CLASSIFICATION/CULTIVAR DENOMINATION

*Euphorbia pulcherrima* Willd. cultivar Giant Red.

BACKGROUND OF THE INVENTION

The present Invention relates to a new and distinct cultivar of Poinsettia plant, botanically known as *Euphorbia pulcherrima* Willd., and hereinafter referred to by the name 'Giant Red'.

The new Poinsettia is a product of a planned breeding program conducted by the Inventor in Gönnebek, Germany. The objective of the breeding program is to create new Poinsettia cultivars with vigorous growth habit, thick stems and attractive flower bract coloration.

The new Poinsettia originated from a cross-pollination made by the Inventor in December, 1997 of an unnamed proprietary selection of *Euphorbia pulcherrima* Willd., not patented, as the female, or seed, parent, with the *Euphorbia pulcherrima* Willd. cultivar Supjibi, disclosed in U.S. Plant Pat. No. 6,592, as the male, or pollen, parent. The cultivar Giant Red was discovered and selected by the Inventor as a flowering plant within the progeny of the stated cross-pollination in a controlled environment in Gönnebek, Germany. The selection of this plant was based on its attractive flower bract coloration and uniform plant habit.

Asexual reproduction of the new Poinsettia by vegetative terminal cuttings taken at Gönnebek, Germany since 1998, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Giant Red'. These characteristics in combination distinguish 'Giant Red' as a new and distinct cultivar:

1. Inflorescences with red-colored flower bracts.
2. Dark green-colored leaves.
3. Uniform and rounded plant habit.
4. Early flowering; response time, about eight weeks.
5. Excellent post-production longevity.

Plants of the new Poinsettia differ primarily from plants of the female parent selection in plant form.

Plants of the new Poinsettia can be compared to plants of the male parent, the cultivar Supjibi. In side-by-side comparisons conducted in Gönnebek, Germany, plants of the new Poinsettia differed primarily from plants of the cultivar Supjibi in the following characteristics:

1. Plants of the new Poinsettia had stronger stems than plants of the cultivar Supjibi.
2. Plants of the new Poinsettia had smaller flower bracts than plants of the cultivar Supjibi.
3. Plants of the new Poinsettia had darker red-colored flower bracts than plants of the cultivar Supjibi.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph at the top of the sheet comprises a side perspective view of a single flowering plant of 'Giant Red' grown in a container.

The photograph at the bottom of the sheet comprises a close-up view of a typical inflorescence and leaves of a plant of 'Giant Red'.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Gönnebek, Germany during the fall under commercial practice in a glass-covered greenhouse with day temperatures averaging about 20° C. and night temperatures averaging about 18° C. Single plants were grown in 24-cm pots and pinched once. Plants were exposed to long day/short night conditions for 12 weeks, then flowered under short day/long night conditions. Plants were about 20 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar Giant Red.

Parentage:

*Female parent.*—Unnamed proprietary selection of *Euphorbia pulcherrima* Willd., not patented.

*Male parent.*—*Euphorbia pulcherrima* Willd. cultivar Supjibi, disclosed in U.S. Plant Pat. No. 6,592.

Propagation:

*Type cutting.*—Vegetative terminal cuttings.

*Time to produce a rooted young plant.*—About 35 days at 20° C.

*Root description.*—Thick, fibrous and white in color.

*Rooting habit.*—Freely branching.

Plant description:

*Plant form.*—Inverted triangle, top of plant rounded.

*Growth habit.*—Upright and uniform plant habit.

*Plant height.*—About 40 to 50 cm.

*Plant diameter or spread.*—About 50 to 60 cm.

*Lateral branch description.*—Quantity per plant: About six to ten lateral branches develop after pinching. Length: About 20 to 35 cm. Diameter: About 5 mm. Internode length: About 0.8 to 4 cm. Texture: Smooth, glabrous. Color: 147B.

*Foliage description.*—Arrangement: Alternate, single. Quantity of leaves per lateral branch: About 15 to 25. Length: About 11 to 16 cm. Width: About 6 to 10 cm. Shape: Mostly ovate. Apex: Acuminate. Base: Obtuse. Margin: Entire with slight irregular lobing. Venation pattern: Pinnate. Texture, upper and lower surfaces: Glabrous, smooth. Surface: Rugose. Color: Young foliage, upper surface: 137A. Young foliage, lower surface: 137C. Fully expanded foliage, upper surface: Darker than 147A. Fully expanded foliage, lower surface: 137B. Venation, upper and lower surfaces: 138B. Petiole: Length: About 4 to 9 cm. Diameter: About 3 to 4 mm. Texture, upper and lower surfaces: Glabrous, smooth. Color, upper and lower surfaces: 184B.

Inflorescence description:

*Inflorescence type and habit.*—Inflorescences are compound corymbs of cyathia with colored flower bracts subtending the cyathia. Inflorescences are not fragrant. Inflorescences persistent.

*Natural flowering season.*—Autumn/winter in Northern Hemisphere. Flower initiation and development is induced under long nyctoperiod conditions. Response time, about eight weeks.

*Post-production longevity.*—Plants of the new Poinsettia maintain good substance and bract color for about two months under interior conditions.

*Quantity of inflorescences per plant.*—One per lateral branch, about six to ten.

*Inflorescence size.*—Diameter: About 16 to 26 cm. Height (depth): About 5 to 6 cm.

*Flower bracts.*—Quantity of flower bracts per inflorescence: About 12 to 15. Length: About 6 to 12 cm. Width, largest bracts: About 4 to 9 cm. Shape: Mostly ovate. Apex: Cuspidate. Base: Obtuse. Margin: Entire with some irregular lobing. Texture, upper and lower surfaces: Glabrous, velvety. Surface: Rugose. Orientation: Mostly horizontal. Color: Developing bracts, upper and lower surfaces: Closest to 53C. Fully developed bracts, upper surface: 45A; color fading to 45C with subsequent development. Fully developed bracts, lower surface: 53C. Venation, upper and lower surfaces: Same as lamina. Bract petiole: Length: About 5 to 10 mm. Diameter: About 2 mm. Texture, upper and lower surfaces: Glabrous, smooth. Color, upper and lower surfaces: 184B.

*Cyathia.*—Quantity of cyathia per corymb: About ten. Diameter of cyathia cluster: About 4 cm. Length: About 8 to 12 mm. Diameter: About 5 to 6 mm. Shape: Ovoid. Color, immature: 146D. Color, mature: 146C. Nectaries: Quantity of nectaries per cyathium: One. Length: About 5 mm. Color: 146D.

Disease/pest resistance: Resistance to pathogens and pests common to Poinsettias has not been observed on plants grown under commercial conditions.

Temperature tolerance: Plants of the new Poinsettia have been observed to tolerate temperatures from 12 to 35° C.

It is claimed:

1. A new and distinct cultivar of Poinsettia plant named 'Giant Red', as illustrated and described.

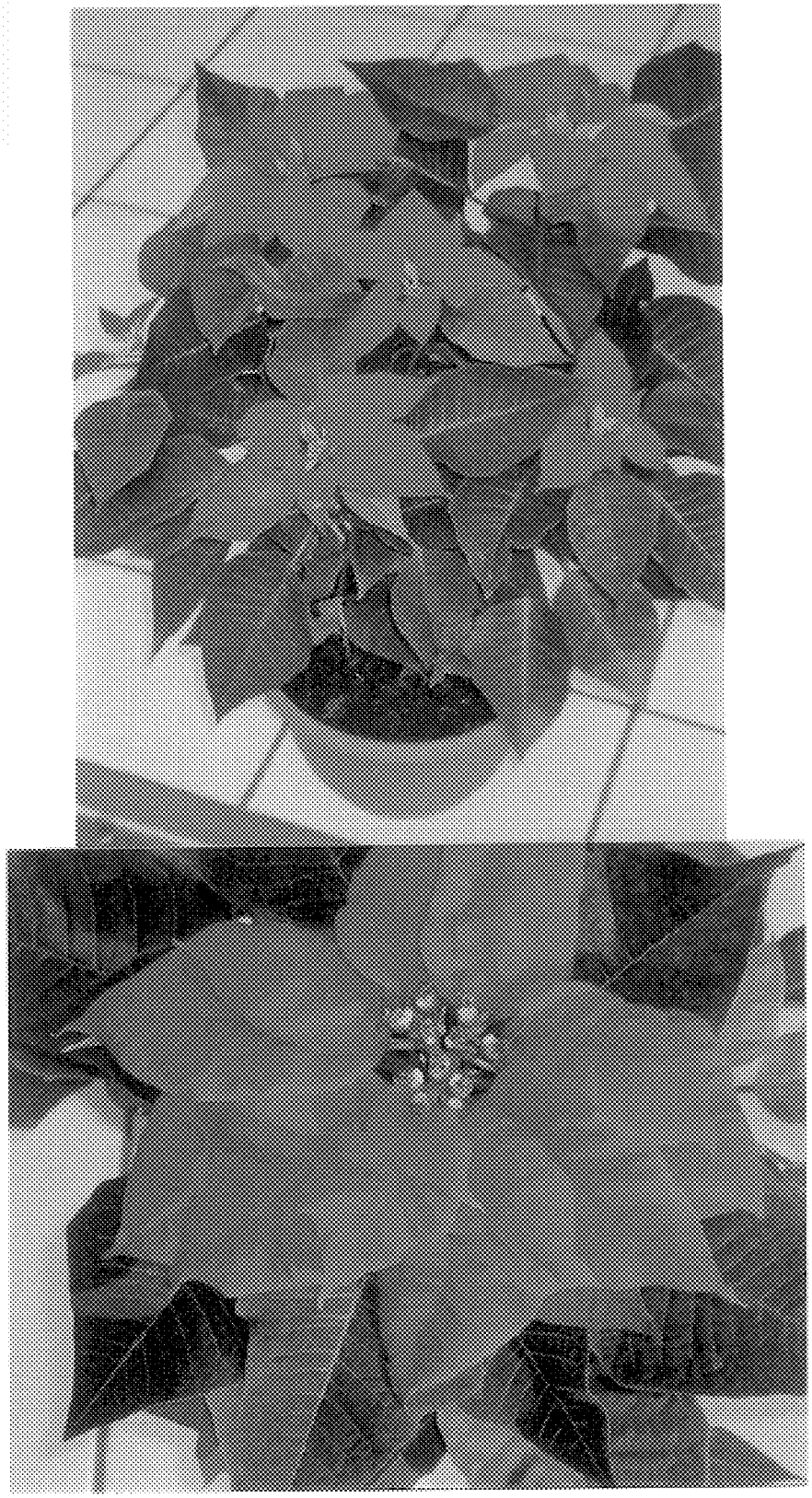

* * * * *